(12) United States Patent
Brengartner et al.

(10) Patent No.: US 10,401,215 B2
(45) Date of Patent: Sep. 3, 2019

(54) METHOD AND DEVICE FOR MONITORING A PROCESS VARIABLE WITH VIBRONIC SENSOR

(71) Applicant: Endress + Hauser GmbH + Co. KG, Maulburg (DE)

(72) Inventors: Tobias Brengartner, Emmendingen (DE); Lukas Gersbacher, Zell i. W. (DE)

(73) Assignee: ENDRESS+HAUSER SE+CO.KG, Maulburg (DE)

( * ) Notice: Subject to any disclaimer, the term of this patent is extended or adjusted under 35 U.S.C. 154(b) by 522 days.

(21) Appl. No.: 14/881,370

(22) Filed: Oct. 13, 2015

(65) Prior Publication Data

US 2016/0109285 A1 Apr. 21, 2016

(30) Foreign Application Priority Data

Oct. 15, 2014 (DE) .......................... 10 2014 114 943

(51) Int. Cl.
*G01H 11/06* (2006.01)
*G01F 1/66* (2006.01)
(Continued)

(52) U.S. Cl.
CPC .............. *G01H 11/06* (2013.01); *G01F 1/20* (2013.01); *G01F 1/66* (2013.01); *G01F 23/0069* (2013.01);
(Continued)

(58) Field of Classification Search
CPC ......... G01H 11/06; G01F 23/296; G01F 1/66; G01F 23/284; G06F 19/00
See application file for complete search history.

(56) References Cited

U.S. PATENT DOCUMENTS 3,668,570 A * 6/1972 Lautier ................ H03H 19/002
327/553
5,555,190 A * 9/1996 Derby ................... G01F 1/8431
702/106
(Continued)

FOREIGN PATENT DOCUMENTS

CN        10 3403533 A      11/2013
DE            69723706 T2     6/2004
DE      10 2009 028022 A1    2/2011

OTHER PUBLICATIONS

Search Report dated May 13, 2016 issued in corresponding European application No. 15 18 5571.
(Continued)

*Primary Examiner* — Michael Jung
(74) *Attorney, Agent, or Firm* — Bacon & Thomas, PLLC

(57) ABSTRACT

A method to determine and/or monitor at least one process variable of a medium with at least one vibration-capable unit. The vibration-capable unit is excited to mechanical vibrations by means of an electrical excitation signal of an adjustable frequency; wherein the mechanical vibrations are transduced into a received electrical signal, which is characterized at least by a frequency and/or a phase and/or an amplitude. The excitation signal is generated based on the received signal; wherein the voltage values of the received signal are sampled at specified predetermined points in time, starting from the excitation signal. The real part and the imaginary part of the received signal are determined from the sampled voltage values of the received signal by means of a Goertzel algorithm; wherein at least one Goertzel coefficient—in particular the number of the sample values and/or an operating frequency and/or a sample frequency—is provided for performing the Goertzel algorithm. At least the current phase and/or the current amplitude of the received signal are calculated from the real part and the
(Continued)

imaginary part of the received signal; wherein the frequency of the excitation signal is adjusted such that a predeterminable phase shift is present between the excitation signal and the received signal; and wherein the at least one process variable is determined.

14 Claims, 4 Drawing Sheets

(51) Int. Cl.
  *G01F 23/284*  (2006.01)
  *G01F 23/00*  (2006.01)
  *G01F 23/296*  (2006.01)
  *G01N 9/00*  (2006.01)
  *G01F 1/20*  (2006.01)

(52) U.S. Cl.
  CPC .......... *G01F 23/284* (2013.01); *G01F 23/296* (2013.01); *G01F 23/2967* (2013.01); *G01N 9/002* (2013.01); *G01N 2009/006* (2013.01)

(56) References Cited

U.S. PATENT DOCUMENTS

| | | | |
|---|---|---|---|
| 5,734,112 A | 3/1998 | Bose | |
| 5,818,296 A * | 10/1998 | Lee | H04L 27/148 329/300 |
| 2012/0279283 A1* | 11/2012 | Brengartner | G01F 23/2961 73/54.41 |
| 2013/0036816 A1* | 2/2013 | Urban | G01F 23/296 73/32 A |
| 2013/0080081 A1* | 3/2013 | Dugger | G01F 1/667 702/48 |
| 2013/0173680 A1* | 7/2013 | Lei | G06F 17/141 708/405 |
| 2015/0233750 A1* | 8/2015 | Malinovskiy | G01S 7/354 342/124 |
| 2016/0161310 A1* | 6/2016 | Leaders | G01F 1/663 702/48 |

OTHER PUBLICATIONS

German Search Report, German Patent Office, Munich, DE, Nov. 17, 2014.

* cited by examiner

METHOD AND DEVICE FOR MONITORING A PROCESS VARIABLE WITH VIBRONIC SENSOR

TECHNICAL FIELD

The invention concerns a method and a device for monitoring at least one process variable of a medium with at least one unit capable of vibration.

BACKGROUND DISCUSSION

For example, in the case of fill level measurement apparatuses, such devices—also designated as vibronic sensors—have e.g. an oscillation fork, a single rod or a membrane as a vibration-capable unit. In operation, this vibration-capable unit is excited to mechanical vibrations by means of an electromechanical transducer unit, which may in turn by a piezoelectric actuator or an electromagnetic actuator, for example. In the case of flow rate measurement apparatuses, however, the vibration-capable unit may also be designed as a vibration-capable tube through which the respective medium flows, for example in a measurement apparatus operating according to the Coriolis principle. Naturally, it is understood that additional possibilities which likewise fall under the present invention are also present in addition to the cited examples of a vibration-capable unit and an electromechanical transducer unit.

Corresponding field apparatuses are manufactured in a wide variety by the applicant and—for example in the case of fill level measurement apparatuses—are distributed under the designation LIQUIFANT and/or SOLIPHANT. The underlying measurement principles are known in principle from a plurality of publications. The excitation of the vibration-capable unit to mechanical vibrations by means of the electromechanical transducer unit for the most part takes place via an analog electrical oscillating circuit. The electromechanical transducer unit excites the vibration-capable unit to mechanical vibrations by means of an electrical excitation signal. Conversely, the electromechanical transducer unit may receive the mechanical vibrations of the vibration-capable unit and transduce them into a received electrical signal. The electromechanical transducer unit accordingly comprises either a separate actuator unit and a separate receiver unit, or a combined actuator/receiver unit.

The actuator/receiver unit is thereby part of a control circuit integrated into an electronic unit, which control circuit adjusts the excitation signal such that a predeterminable phase shift is present between the excitation signal and received signal. For example, the oscillating circuit condition, according to which all phases occurring in the oscillating circuit result in a multiple of 360°, must be satisfied for a resonant vibration.

Both the excitation signal and the received signal are characterized by their frequency, amplitude and/or phase. Changes in these variables are accordingly typically used to determine the respective process variable, for example a predetermined fill level of a medium in a container, or also the density and/or viscosity of a medium, or the flow rate of a medium through a tube. In the case of a vibronic point level switch for fluids, for example, a differentiation is made as to whether the vibration-capable unit is covered by the fluid or vibrates freely. These two states—the free state and the covered state—are thereby differentiated using different resonance frequencies, i.e., a frequency shift, for example. The density and/or viscosity in turn can be determined with such a measurement apparatus only given an at least partial coverage with the medium.

In the prior art, both analog and digital methods for the excitation of the vibration-capable unit have been known, wherein the digital excitation is characterized by its more universal possibilities for use. However, this in turn often disadvantageously involves a markedly higher power consumption for the respective measurement apparatus. Therefore, a digital excitation method with a low power consumption would be desirable.

For example, in German Patent, DE102009026685A1 a method has become known for digitally controlled excitation of a vibronic sensor which is based on a forced excitation with a defined frequency. In order to find the excitation frequency for the excitation signal at which the predeterminable phase shift is present, a frequency sweep is implemented, and the frequency corresponding to the predeterminable phase shift is determined. An advantageous development of this method is the subject matter of German Patent, DE102009028022A1, in which the evaluation of the received signal is simplified in that the received signal is sampled and evaluated phase-selectively only at specific points in time. An additional further development is described in German Patent, DE1020110075113A1 and lies in conducting two frequency sweeps in different travel directions with subsequent mean value calculation, in order to increase the measurement precision. However, measurement apparatuses which are designed to execute the cited methods are not, without additional steps, suitable for operation of the measurement apparatus via a 4-20 mA interface or a NAMUR interface.

An additional digital possibility for a vibronic sensor to regulate the phase shift between the excitation signal and received signal at a predeterminable value is disclosed in German Patent, DE00102010030982A1. The method described there is based on the functional principle of a phase control loop (phase locked loop, PLL), and is already optimized for a reduction of the power consumption. For such an arrangement, at least one phase detector is required which has a decisive influence on the robustness as well as on the precision of the control loop. So that the evaluation may take place stably, it must additionally be ensured that the amplitude of the excitation signal is kept to a constant value. However, this is comparably elaborate in practice.

SUMMARY OF THE INVENTION

The present invention is based on the object to provide a method and a device that enable the phase shift between the excitation signal and received signal to be set reliably and simply to a predeterminable value, given a low power consumption.

According to the invention, the object is achieved via a method to determine and/or monitor at least one process variable of a medium with at least one vibration-capable unit, wherein the vibration-capable unit is excited to mechanical vibrations by means of an electrical excitation signal of an adjustable frequency, wherein the mechanical vibrations are transduced into a received electrical signal, which received signal is characterized by a frequency and/or a phase and/or an amplitude, wherein the excitation signal is generated based on the received signal, wherein the voltage values of the received signal are sampled at specified predetermined points in time, starting from the excitation signal, wherein the real part and imaginary part of the received signal are determined from the sampled voltage values of the received signal by means of a Goertzel algorithm, wherein at least one Goertzel coefficient—in particular the number of the sample values and/or an operating frequency and/or a sample frequency—is provided for performing the Goertzel algorithm, wherein at least the current phase and/or the current amplitude of the received signal are calculated from the real part and imaginary part of the received signal, wherein the frequency of the excitation signal is adjusted such that a predeterminable phase shift is present between the excitation signal and received signal, and wherein the at least one process variable is determined.

The Goertzel algorithm has its origin in discrete Fourier transformation (DFT). Typically, a fast Fourier transformation (FFT)—a significant simplification of the DFT, for example as described in the German publications DE10201101667A1 or DE10203461A1, both of which deal with vibronic sensors—is used for frequency analysis. However, in other fields of process engineering, an FFT is also used repeatedly, for example in the German publications, DE69730416T2 or DE102004030740A1. Instead of an FFT, the Goertzel algorithm is now to be used, which is motivated by the following context:

The Goertzel algorithm in principle represents a new simplification relative to an FFT if it is desired to consider the DFT of a signal for only one or a few spectral components k. Namely, the Goertzel algorithm delivers the discrete Fourier coefficients at a specific frequency as initial sample values. Accordingly, its use only makes sense if the frequency range for the respective signal is known precisely.

In the case of a forced excitation of a vibronic sensor, the excitation signal is known and the received signal is in turn evaluated with regard to the frequency of the excitation signal. By the artful combination of the individual components of the oscillation circuit and/or control circuit, and by the artful selection of the respective parameters for the Goertzel algorithm, the so-called Goertzel coefficient, it may therefore be advantageous to use the Goertzel algorithm use instead of an FFT. Via a corresponding evaluation method, the number of necessary calculation operations is then markedly reduced.

Finally, the power consumption for a correspondingly designed measurement apparatus may become markedly lower via the application of the Goertzel algorithm, which in particular is advantageous for the implementation of 4-20 mA interfaces or NAMUR interfaces and/or the use of the measurement apparatus in an explosion-susceptible atmosphere.

The Goertzel coefficients are thereby provided by: the number of sample values N; the spectral component $f_k$ that is to be considered, which spectral component represents the operating frequency of the Goertzel algorithm; and the sample frequency fs which is provided by the inverse of the sample rate $T_S$. From these values, what is known as the Goertzel window additionally results, which Goertzel window is determined from the product of the number of sample values N and the sampling interval T, and accordingly is a measure of the frequency resolution.

In the selection of the Goertzel coefficients, specific conditions should be complied with in order to achieve an optimally precise evaluation.

The Goertzel coefficients are linked together via the equation $$f_k = k \frac{f_S}{N}.$$

Normally, a sampling frequency $f_S$ is defined first, and the factor k is subsequently determined, such that the operating frequency $f_k$ corresponds to the excitation signal.

However, in particular given a vibronic sensor in which the excitation signal is known, it is advantageous if the working frequency is set to the frequency of the excitation signal. This procedure has the consequence that the sampling frequency $f_S$ is continuously adapted instead of the factor k.

Furthermore, it is advantageous if the sampling frequency is set to a whole-number multiple n of the frequency of the excitation signal. This may lead to a simplification of the computing effort for the Goertzel algorithm. In particular, if the working frequency is additionally set to the frequency of the excitation signal, the correlation k=N/n results for the factor k.

Moreover, it is advantageous if a whole-number multiple of a period of the excitation signal is selected for the number of sample values. What are known as cut-off errors—also known as latch-up effects—may be avoided in this way.

An additional and distinct reduction of the computing effort, and accordingly the power consumption of a corresponding measurement apparatus, may be achieved via the suitable and artful establishment of additional conditions for the respective Goertzel coefficients.

In a particularly preferred embodiment, two or four times the frequency of the excitation signal is set as the sampling frequency. This selection is particularly advantageous. Namely, it has the effect of simplifying inherently computationally complex trigonometric terms within the algorithm to constant values.

In a preferred embodiment, the Goertzel algorithm is performed over multiple periods of the excitation signal. The more periods that are run, the more robustly the amplitude detection and/or phase detection.

Furthermore, it is advantageous if the excitation signal is a square wave signal or a sinusoidal signal.

Measures are also necessary with which the predeterminable phase shift between the excitation signal and received signal may be set. Both signals show a periodic chronological behavior which may be utilized to adjust a predeterminable phase shift.

In a particularly preferred embodiment, the predeterminable phase shift is accordingly set using the quotients of the number of sample values and the sampling frequency by means of a time shift in relation to the excitation signal. The phase shift is thus generated via an adjustment of the Goertzel window in relation to the excitation signal.

It is thereby advantageous if the predeterminable phase shift is 90°. A resonant excitation takes place in this way while fulfilling the oscillating circuit condition.

In a further preferred embodiment, a measurement period is subdivided into at least two time intervals, wherein respectively a first predeterminable phase shift is set in a first time interval, and a second predeterminable phase shift is set in a second time interval. This procedure is advantageous for the determination of the viscosity of the medium. To accomplish this, the received signal is namely evaluated with regard to different phase shifts relative to the excitation signal.

In a further preferred embodiment, a function defined by the quotient of the real part and the amount of the imaginary part of the received signal, or the inverse of this function for the control deviation, is used to set the predeterminable phase shift. This represents a simplification of the calculation of the current phase shift relative to the mathematically exact method.

It is thereby advantageous if the control deviation is limited, in particular to +/−1.

The object according to the invention is also achieved via a device to determine and/or monitor at least one process variable of a medium with at least one vibration-capable unit: with an electromechanical transducer unit which is designed to excite the mechanical vibration-capable unit to mechanical vibrations based on an electrical excitation signal of an adjustable frequency, and to receive the mechanical vibrations and transduce them into a received electrical signal, which received signal is characterized at least by a frequency and/or a phase and/or an amplitude, and with an electronic unit with a microprocessor which is designed: to generate the electrical excitation signal based on the received signal, to sample the voltage values of the received signal at defined predetermined points in time, to determine the real part and imaginary part of the received signal from the sampled voltage values of the received signal by means of a Goertzel algorithm, wherein at least one Goertzel coefficient—in particular the number of the sample values, and/or a working frequency, and/or a sample frequency—is provided for performing the Goertzel algorithm, to calculate at least the current phase and/or the current amplitude of the received signal from the real part and imaginary part of the received signal, and with a control unit that is designed to set the frequency of the excitation signal such that a predeterminable phase shift is present between the excitation signal and received signal, and which electronic unit is designed to determine the at least one process variable.

The device according to the invention is thus designed such that it is suitable for implementation of the method according to the invention.

In a particularly preferred embodiment, the microprocessor is a low-power microprocessor. The power consumption by the electronic unit may thus be minimized relative to a central processing unit. In particular, the combination of a corresponding low-power microprocessor with a Goertzel algorithm in which the sampling frequency is set to two or four times the frequency of the excitation signal allows for the first time the implementation of a NAMUR interface for a corresponding field apparatus.

In a further particularly preferred embodiment, an anti-aliasing filter is provided, in particular an adaptive switched capacitor filter. A particular function is accorded to this filter in this context. According to what is known as the Nyquist-Shannon sampling theorem, the sampling frequency should be selected such that $f_s > 2f_a$ applies, wherein $f_a$ corresponds to the signal with the largest spectral component k. Too low a sampling frequency fs disadvantageously has the result that high-frequency portions of the excitation signal are interpreted as having lower frequency, which is also designated as the aliasing effect. In contrast to this, too high a sampling rate leads to large data sets and to a large number of necessary computing operations. A lower sampling frequency fs is thus advantageous with regard to the power consumption. It is thus accordingly advantageous to use an anti-aliasing filter. On the one hand, this improves the robustness of the control loop, and on the other hand it suppresses the respective interference signals resulting due to the selection of a low sampling rate. Since the sampling frequency is on the same order of magnitude as the excitation frequency, and because the detection of the phase shift may not be affected by the filter, an adaptive switched capacitor filter is particularly suitable. This allows a good suppression of the interference frequencies without affecting the detection of the phase. The Nyquist-Shannon sampling theorem may then be maintained via suitable adaptation of the working frequency of the switched capacitor filter. The integration of the SC filter is thus also advantageous in particular with regard to a low power consumption since a high precision may be achieved via the filter, even if the sampling frequency is set to two or four times the frequency of the excitation signal.

In addition to the interference signals resulting due to the selection of a low sampling rate, the switched capacitor filter generally supplies very good interference signal suppression and represents a cost-effective realization of the same. This is also described in German Patent, DE00102010028303A1.

In a preferred embodiment, the at least one process variable is provided by the fill level, the density, or the density of the medium in a container, or by the volume flow rate of the medium through a tube.

In a further preferred embodiment, an electromechanical transducer unit is provided which is designed to excite the vibration-capable unit to mechanical vibrations. It is thereby advantageous if the electromechanical transducer unit is provided by a piezoelectric actuator or an electromagnetic actuator.

BRIEF DESCRIPTION OF THE DRAWINGS

The invention as well as its advantageous embodiments are described in detail in the following with reference to FIGS. 1-5. Illustrated are.

DETAILED DISCUSSION IN CONJUNCTION WITH THE DRAWINGS

Figure 1:
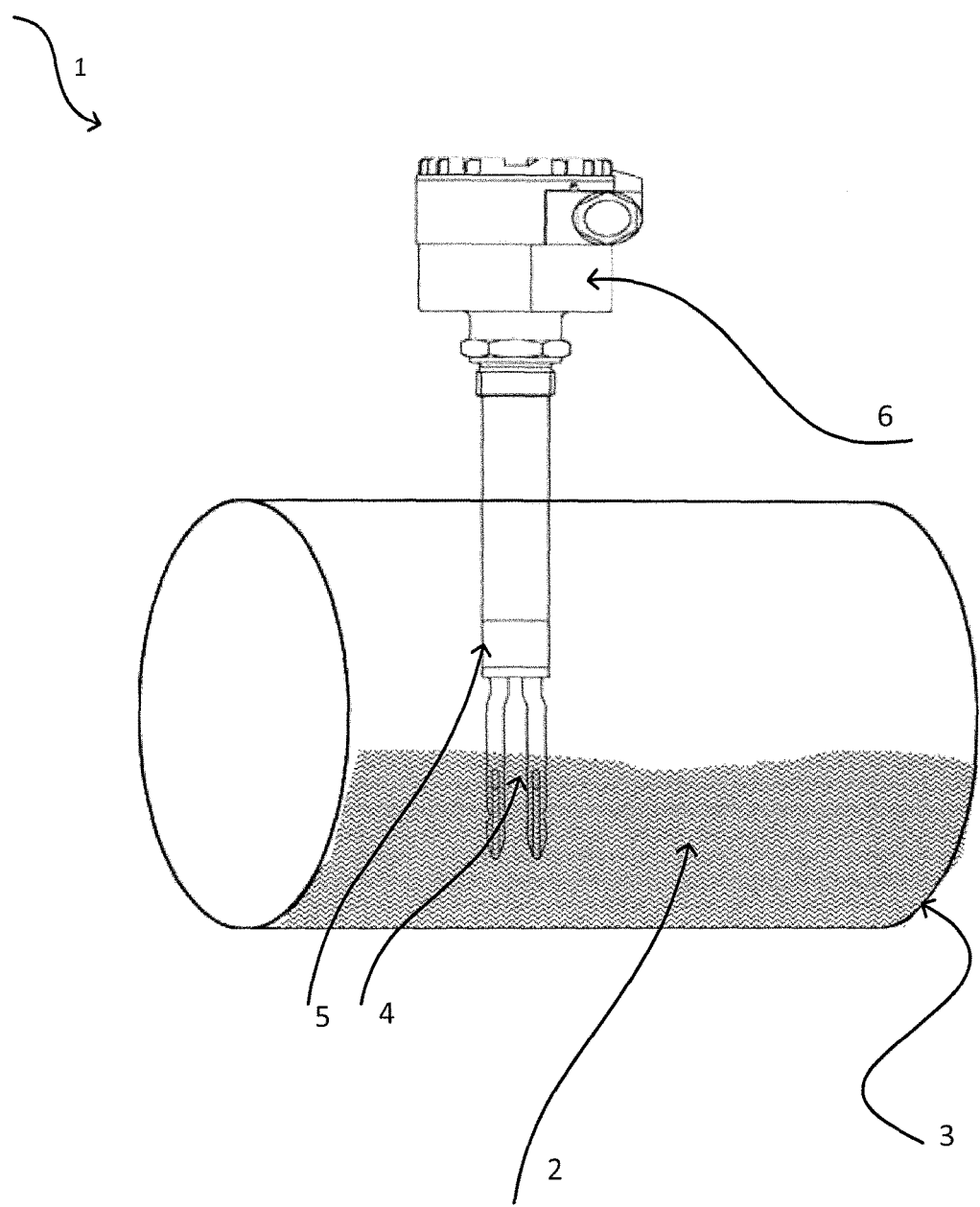
FIG. 1: is a schematic drawing of a vibronic sensor according to the prior art.

A vibronic sensor 1 is shown in FIG. 1. A vibration-capable unit 4 is depicted in the form of an oscillating fork which submerges partially into a medium 2 which is located in a container 3. The vibration-capable unit is excited to mechanical vibrations by means of the electromechanical transducer unit 5 and may, for example, be a piezoelectric stack actuator or bimorph actuator. However, it is naturally understood that other embodiments of a vibronic sensor also fall under the invention. Furthermore, an electronic unit 6 is depicted by means of which the signal evaluation and/or signal feed takes place. A block diagram of the necessary components of an electronic unit according to the invention is the subject matter of FIG. 2.

The sensor element 7, comprised of the vibration-capable unit 4 and the electromechanical transducer unit 5 from FIG. 1, is supplied with an excitation signal $U_A$. Conversely, the electromechanical transducer unit 5 generates, from the mechanical vibrations, a received electrical signal $U_E$, upon which may be superimposed interference signals $U_D$ which are filtered out by means of an adaptive switched capacitor (SC) filter 8. This serves as an anti-aliasing filter and is especially suitable due to the power consumption requirements of a corresponding measurement apparatus. Furthermore, its adaptive functionality allows the known excitation signal to be followed.

Within the microprocessor 9—in particular a low-power microprocessor—the filtered received signal first traverses an analog/digital converter (ADC) 10 and is subsequently evaluated by means of a Goertzel algorithm 11 with regard to its phase $\varphi_A$ and amplitude $A_A$. The frequency of the received signal is set by means of a PI controller 12 so that a predeterminable phase shift $\Delta\varphi$ is present between the excitation signal and received signal. Finally, the excitation signal is generated by means of a digitally controlled oscillator (DCO), which excitation signal traverses a digital/analog converter (DAC) 13 and again serves to charge the sensor element 7.

The Goertzel algorithm is known per se and, for example, is described in "Digitate Signalverabeitung" [Digital Signal Processing] by D. Ch. Von Grüningen, published in the 3rd edition by Fachbuchverlag Leipzig in 2004.

The transfer function $H_k(z)$ for a second-order Goertzel algorithm is provided by $$H_k(z) = \frac{1 - W_N^k z^{-1}}{1 - az^{-1} + z^{-2}}$$

with $$W_N = e^{\frac{-j2\pi}{N}}$$

and $a = 2\cos(k2\pi/N)$. The Goertzel algorithm accordingly consists of a recursive branch and non-recursive branch. The recursive branch represents a resonator through which all sampled values pass while, after N sample values, the non-recursive branch is traversed once, and as a result supplies the real part and imaginary part of the excitation signal from which the respective variables may be calculated via additional mathematical relations. For this reason, the Goertzel algorithm may also be viewed as a decimating digital filter which, after N sample values, delivers an output value which corresponds to the DFT coefficient at point k. After the calculation of the respective output value, the initial conditions are each reset to zero, and an additional calculation may be started. Since the recursive branch describes a resonator structure, the working frequency of the Goertzel algorithm is often also designated as a resonance frequency.

In practice, the process normally takes place such that the sampling frequency $f_S$ is defined first, and the factor k is subsequently determined via the equation $$f_k = k\frac{f_S}{N}$$

such that the working frequency $f_k$ corresponds to the excitation signal. If k is a whole number, the algorithm is called a "normal Goertzel algorithm"; given a real k, the algorithm is what is known as a "generalized Goertzel algorithm".

Figure 2:
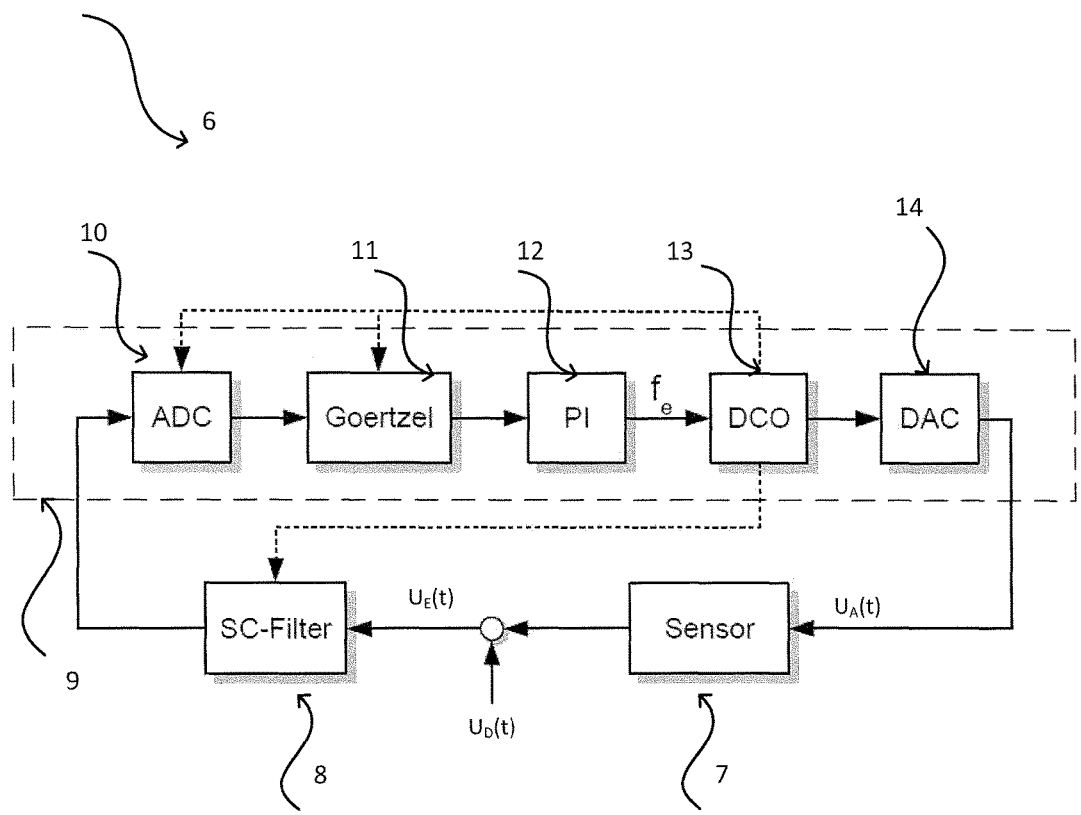
FIG. 2: is a block diagram of an electronic unit according to the invention.

A special Goertzel algorithm optimized with regard to a forcibly excited system and with regard to low power consumption is illustrated in FIG. 2, likewise in the form of a block diagram. The necessary measures for optimization are based on an intelligent selection of the sampling frequently and number of sample values. Since the excitation signal is known given a forced excitation, as is typical for vibronic sensors, and because the received signal is evaluated with regard to the frequency of the excitation signal, the sampling rate $T_S$ may be selected intelligently. The Goertzel window as well as the position of the sample values N are then directly coupled to the excitation signal. This has the result that, instead of the factor k, the sampling frequency is adapted continuously such that the working frequency of the Goertzel algorithm is adapted to the signal frequency.

Given a suitable selection of the sampling frequency, the necessary computing operations of the Goertzel algorithm are significantly simplified. In this regard, the sampling frequency is selected so that it amounts to a whole-number multiple of the excitation frequency $f_{An}$:

$$f_S = nf_{An}.$$

Consequently, for the working frequency $f_k$ $$f_k = k\frac{nf_{An}}{N}$$

and, under consideration of the condition $f_k = f_{An}$, $$k = \frac{N}{n}.$$

If n=4 is now selected in particular, which corresponds to a sampling frequency that is four times higher than the excitation signal, a decisive simplification results for the respective calculation operations to be performed. The trigonometric terms "a" namely become a constant. In contrast to the general Goertzel algorithm, only additions and subtractions are accordingly executed in the recursive branch, which in turn has a decisive advantage for the implementation of the algorithm in a low-power microcontroller. In particular, exclusively whole-number output values occur given whole-number input values. Since integer values are generated in the ADC, in this case a fixed point arithmetic ultimately does not need to be selected.

The real part and imaginary part of the excitation signal may be measured immediately after N−1 sample values by means of the optimized Goertzel algorithm.

Figure 3A:
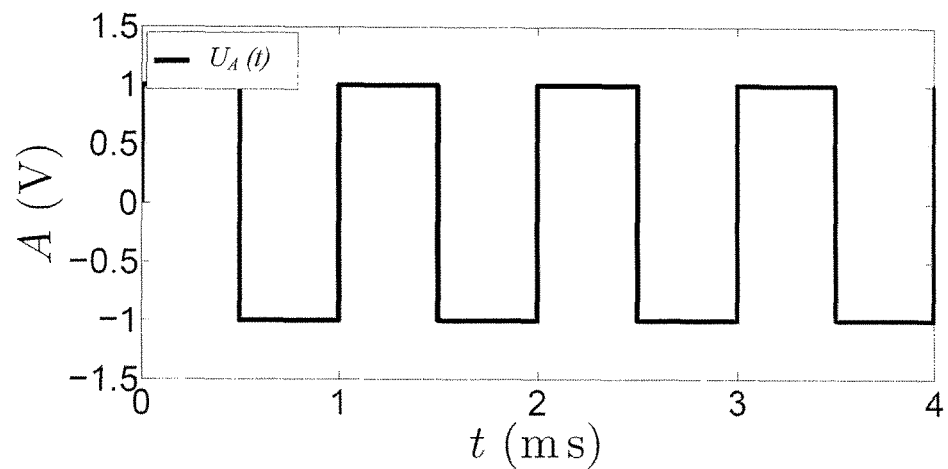
FIG. 3: is a schematic progression of the excitation signal (a) and received signal (b)
Figure 3B:
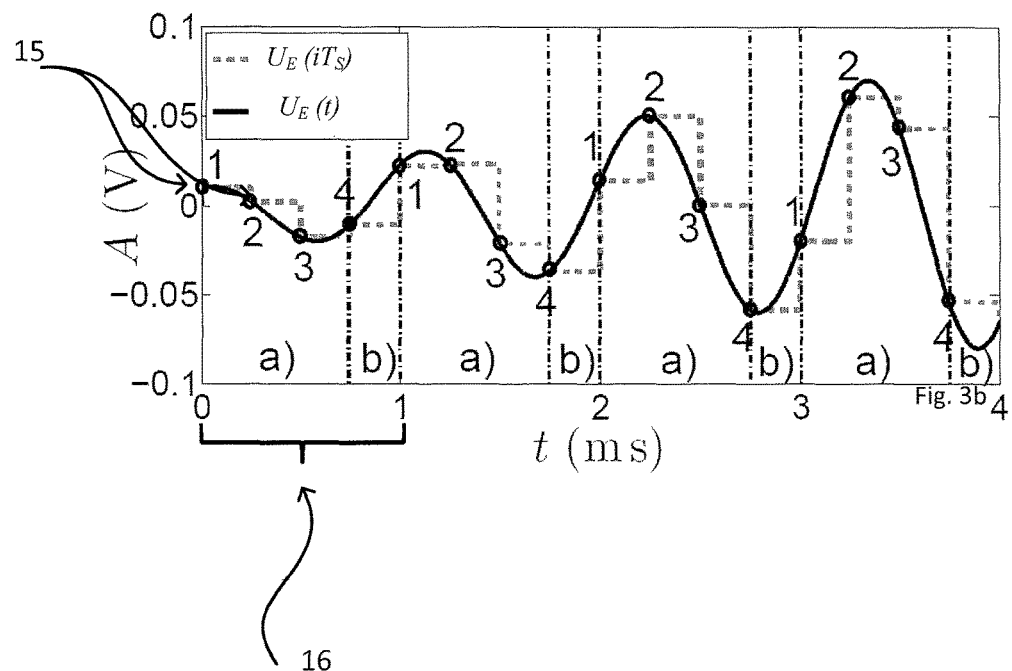

The course of an excitation signal (a) and of a sampled received signal (b) are schematically shown in FIG. 3. The excitation signal in FIG. 3a) is provided by a chronological, periodic square wave signal. Both the sample points in time and the relative position of the Goertzel window are defined using the excitation signal. The received signal—which, in this case, is provided by a sinusoidal signal—is shown in FIG. 3b)

For this example, the length of the Goertzel window 16 amounts to exactly one signal period of the excitation signal, and N=4 was selected for the number of sample values 15 since this selection is particularly advantageous with regard to a reduction of the computing effort. However, it is inherently understood that the length of the Goertzel window 16 may also amount to a different whole-number multiple of the signal period of the excitation signal. In general, the more periods traversed by the recursive branch of the Goertzel algorithm, the more narrowband the response of the resonator structure, and the more robust the phase and/or amplitude detection. On the other hand, the speed of the phase and/or amplitude detection decreases with an increasing number of traversed periods.

The chronological order of the recursive (a) and non-recursive (b) branch of the Goertzel algorithm is plotted in FIG. 3b. Given a length of the Goertzel window which corresponds to N sample values, N−1 values traverse the recursive branch (a), wherein after the N−1 values, the non-recursive branch (b) is traversed once and the real part and imaginary part are calculated, from which in turn the phase information and/or amplitude information may be calculated. It thereby holds true that:

$$\Phi(iT_S) = \arctan\left(\frac{\text{Im}(iT_S)}{\text{Re}(iT_S)}\right),$$

$$A(iT_S) = \frac{2}{N}\sqrt{\text{Im}(iT_S)^2 + \text{Re}(iT_S)^2}$$

The phase thereby needs to be corrected depending on the algebraic sign of the real part and/or imaginary part. In conclusion, the Goertzel algorithm is reset again to the initial conditions.

Figure 4:
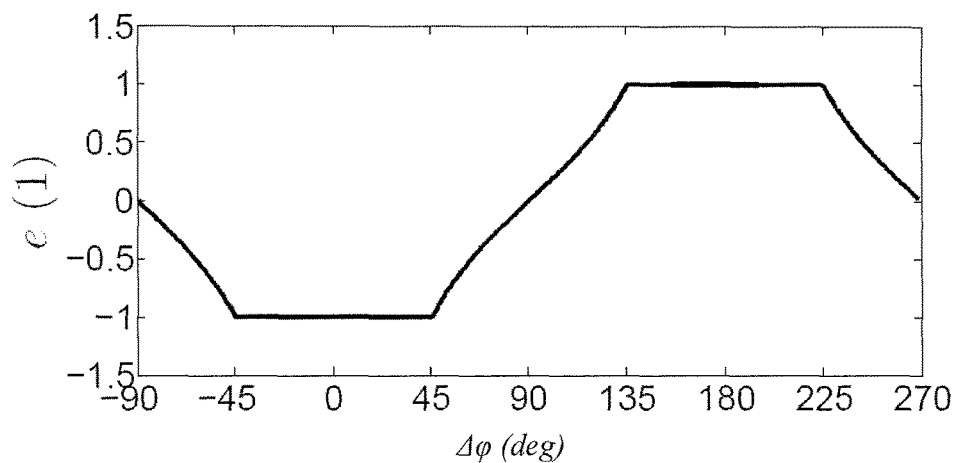
FIG. 4: is a schematic drawing of the curve of the simplified control function.

Since the calculation of the current phase by means of the arc tangent function is very computationally involved, instead of this calculation the quotient of the imaginary part and real part may be used as a control deviation. The corresponding control function is drawn schematically in FIG. 4. The basic idea behind this simplification is that the real part is zero given a phase shift of 90°. It can consequently be used to define the control deviation or, respectively, to regulate the phase. What is known as an error function is accordingly defined as a control deviation, which error function is provided by:

$$e = \frac{\text{Re}}{|\text{Im}|}.$$

Figure 5:
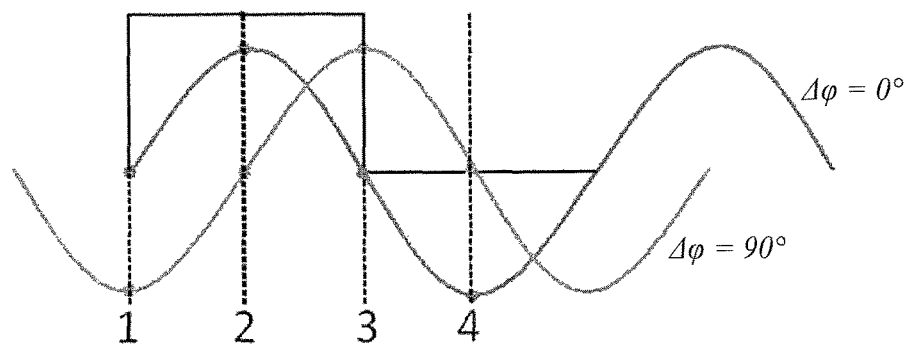
FIG. 5: is an illustration of the adjustment of the predeterminable phase shift.

The imaginary part is thereby likewise considered because, given a phase shift differing from 90°, the real part depends on the amplitude, and therefore also on the imaginary part. That the value of the imaginary part is used in turn serves to cover a maximum range for the phase. It is thereby advantageous to limit the control deviation, in particular to +/−1. It is noted that this definition applies to a cosine signal. The error function must be inverted for a sine signal so that e=0, given a phase shift of Δφ=90°. Finally, the adjustment of the predeterminable phase shift between the excitation signal and received signal is illustrated in FIG. 5. Two excitation signals are shown. The black curve has a phase of φ=0°; the gray curve has a phase of φ=90°. To set a specific, predeterminable phase shift, the location of the Goertzel window is thus modified in terms of its position.

It is now the case that the control function, which represents a function of the phase shift Δφ, is displaced via the adjustment of a phase shift. In order to be able to adjust to a phase shift that differs from 90°, the entire control function must accordingly be displaced analogously along the abscissa, such that e=0 results for the respective predeterminable phase shift. Given this possibility of being able to set a phase shift differing from 90°, the density of the medium may also be determined as, for example, a process variable in addition to a predetermined fill level. Furthermore, the option exists to switch back and forth between two different predeterminable phase shifts. In addition to the density, the viscosity of the medium may thereby also be determined, which results from the frequency difference between the two different phase shifts.

The invention claimed is:

1. A device to determine and/or monitor at least a fill level, a density, a viscosity, or a volume flow rate of a medium, comprising:
   at least one mechanical vibration-capable unit;
   a control unit;
   an electromechanical transducer unit which is designed to excite said at least one mechanical vibration-capable unit to mechanical vibrations based on an electrical excitation signal of an adjustable frequency, and to receive the mechanical vibrations and transduce them into an electrical received signal, which electrical received signal is characterized at least by a frequency and/or a phase and/or an amplitude;
   an electronic unit with a microprocessor which is designed:
   to generate the electrical excitation signal based on the electrical received signal,
   to sample voltage values of the electrical received signal at defined predetermined points in time,
   to determine the real part and imaginary part of the electrical received signal from the sampled voltage values of the electrical received signal by means of a Goertzel algorithm,
   to preset at least a number of sample values and/or a working frequency and/or a sample frequency for performing the Goertzel algorithm,
   to calculate at least a current phase and/or a current amplitude of the electrical received signal from the real part and imaginary part of the electrical received signal; and
   a control unit that is designed to set the frequency of the electrical excitation signal such that a predeterminable phase shift is present between the electrical excitation signal and electrical received signal; and
   said electronic unit is designed to determine the fill level, density, a viscosity, or volume flow rate.

2. The device according to claim 1, wherein, further comprising:
   an adaptive switched capacitor filter.

3. The device according to claim 1, wherein:
   said electromechanical transducer unit is provided by a piezoelectric actuator or an electromagnetic actuator.

4. A method to determine and/or monitor a fill level, a density, a viscosity, or a volume flow rate of a medium with at least one vibration-capable unit, comprising the steps of:
   exciting the vibration-capable unit to mechanical vibrations by means of an electrical excitation signal of an adjustable frequency;
   transducing the mechanical vibrations into electrical received signal, which electrical received signal is characterized at least by a frequency and/or a phase and/or an amplitude,
   generating the electrical excitation signal based on said electrical received signal;
   sampling voltage values of said electrical received signal at specified predetermined points in time, starting from said electrical excitation signal;
   determining the real part and imaginary part of said electrical received signal from the sampled voltage values of said electrical received signal by means of a Goertzel algorithm,
   presetting at least a number of sample values and/or an operating frequency and/or a sample frequency for performing the Goertzel algorithm;

calculating at least a current phase and/or a current amplitude of said electrical received signal from said real part and imaginary part of said electrical received signal; and adjusting the frequency of said electrical excitation signal such that a predeterminable phase shift is present between said electrical excitation signal and said electrical received signal, and determining the fill level, a density, a viscosity, or a volume flow rate based on said received signal.

5. The method according to claim 4, wherein:
a working frequency is set to the frequency of said electrical excitation signal.

6. The method according to claim 5, wherein:
a whole-number multiple of a period of said electrical excitation signal is selected for the number of said sample values.

7. The method according to claim 4, wherein:
a sampling frequency is selected as a whole-number multiple of the frequency of said electrical excitation signal.

8. The method according to claim 7, wherein:
two or four times the frequency of said excitation signal is set as said sampling frequency.

9. The method according to claim 4, wherein:
the Goertzel algorithm is used across multiple periods of said electrical excitation signal.

10. The method according to claim 4, wherein:
said electrical excitation signal is a square wave signal or a sine signal.

11. The method according to claim 4, wherein:
said predeterminable phase shift is set using the quotient from the number of said sample values and said sampling frequency by means of a time shift of said sample values in relation to said excitation signal.

12. The method according to claim 4, wherein:
said predeterminable phase shift is 90°.

13. The method according to claim 4, further comprising the step of:
subdividing a measurement period into at least two time intervals, wherein:
respectively a first predeterminable phase shift is set in a first time interval, and a second predeterminable phase shift is set in a second time interval.

14. The method according to claim 4, wherein:
a function defined by the quotient of the real part and the value of the imaginary part of said received signal, or the inverse of this function for a control deviation, is used to set said predeterminable phase shift.

* * * * *